(12) United States Patent
Tam

(10) Patent No.: US 6,292,525 B1
(45) Date of Patent: Sep. 18, 2001

(54) USE OF HILBERT TRANSFORMS TO SIMPLIFY IMAGE RECONSTRUCTION IN A SPIRAL SCAN CONE BEAM CT IMAGING SYSTEM

(75) Inventor: Kwok Tam, Edison, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 0 days.

(21) Appl. No.: 09/410,235

(22) Filed: Sep. 30, 1999

(51) Int. Cl.[7] ............................................. A61B 6/03
(52) U.S. Cl. ................................ 378/4; 378/15; 378/901
(58) Field of Search ............................ 378/4, 8, 15, 901

(56) References Cited

U.S. PATENT DOCUMENTS

| | | | |
|---|---|---|---|
| 5,926,521 | * | 7/1999 | Tam ........................................... 378/4 |
| 6,018,561 | * | 1/2000 | Tam ........................................... 378/4 |
| 6,078,638 | * | 6/2000 | Sauer et al. ................................. 378/4 |
| 6,084,937 | * | 7/2000 | Tam et al. ................................... 378/4 |
| 6,130,930 | * | 10/2000 | Tam ........................................... 378/4 |

* cited by examiner

Primary Examiner—David V. Bruce
(74) Attorney, Agent, or Firm—Adel A. Ahmed

(57) ABSTRACT

A method and apparatus for three dimensional (3D) computerized tomography (CT) imaging wherein a reconstructed image is developed by calculating along line segments L formed in cone beam data. The endpoints of which are determined by a data combination mask. At source positions near the top and bottom of the ROI, the mask is divided into separate portions using a horizontal line, each having a set of line segments L formed therein. The reconstruction data is calculated by performing one-dimensional (1D) convolving operations of the data along the line segments L, the 1D convolving operation developing an additive contribution to a new projection image. Finally, the new projection image is backprojected into a 3D space, thereby reconstructing a 3D image of the ROI in the object.

21 Claims, 8 Drawing Sheets

USE OF HILBERT TRANSFORMS TO SIMPLIFY IMAGE RECONSTRUCTION IN A SPIRAL SCAN CONE BEAM CT IMAGING SYSTEM

BACKGROUND OF THE INVENTION

1. Field of the Invention

The invention relates generally to a cone beam computed tomography (CT) imaging system, and more specifically to a simplified method and apparatus for image reconstruction in such a system.

2. Description of the Prior Art

Recently a system employing cone beam geometry has been developed for three-dimensional (3D) computed tomography (CT) imaging that includes a cone beam x-ray source and a 2D area detector. An object to be imaged is scanned, preferably over a 360° angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

As well known, and fully described for example in the present inventor's U.S. Pat. No. 5,257,183 entitled METHOD AND APPARATUS FOR CONVERTING CONE BEAM X-RAY PROJECTION DATA TO PLANAR INTEGRAL AND RECONSTRUCTING A THREE-DIMENSIONAL COMPUTERIZED TOMOGRAPHY (CT) IMAGE OF AN OBJECT issued Oct. 26, 1993, incorporated herein by reference, image reconstruction processing generally begins by calculating Radon derivative data from the acquired cone beam data. The Radon derivative data is typically determined by calculating line integrals for a plurality of line segments L drawn in the acquired cone beam data. In the embodiment described in detail in the 5,257,183 patent, Radon space driven conversion of the derivative data is used to develop an exact image reconstruction of a region-of-interest (ROI) in the object.

A cone beam data masking technique which improves the efficiency of the calculation of the Radon derivative data in such a Radon space driven technique is described in the present inventor's U.S. Pat. No. 5,504,792 entitled METHOD AND SYSTEM FOR MASKING CONE BEAM PROJECTION DATA GENERATED FROM EITHER A REGION OF INTEREST HELICAL SCAN OR A HELICAL SCAN, issued Apr. 2, 1996, also incorporated herein by reference. The masking technique facilitates efficient 3D CT imaging when only the ROI in the object is to be imaged, as is normally the case. In the preferred embodiment described therein, a scanning trajectory is provided about the object, the trajectory including first and second scanning circles positioned proximate the top and bottom edges, respectively, of the ROI, and a spiral scanning path is connected therebetween. The scanning trajectory is then sampled at a plurality of source positions where cone beam energy is emitted toward the ROI. After passing through the ROI the residual energy at each of the source positions is acquired on an area detector as a given one of a plurality of sets of cone beam data. Each set of the cone beam data is then masked so as to remove a portion of the cone beam data that is outside a given sub-section of a projection of the ROI in the object and to retain cone beam projection data that is within the given sub-section. The shape of each mask for a given set of cone beam data is determined by a projection onto the detector of the scan path which is above and below the source position which acquired the given set of cone beam data. The masked (i.e., retained) cone beam data is then processed so as to develop reconstruction data An exact image of the ROI is developed by combining the reconstruction data from the various source positions which intersect a common integration plane. Hence, the masks are commonly referred to as "data-combination" masks.

Data-combination masks can also be used to improve the efficiency of the calculation of the derivative data in a detector data driven technique, such as the simplified ramp filter technique described in the present inventor's U.S. Pat. No. 5,881,123 entitled SIMPLIFIED CONE BEAM IMAGE RECONSTRUCTION USING 3D BACKPROJECTION, issued Mar. 9, 1999, also incorporated herein by reference. This simplified technique reconstructs the image using 2D approximation data sets formed by ramp filtering the masked cone beam data in the direction of the projection of a line drawn tangent to the scan path at the source position that acquired that set of cone beam data. Although this technique is less complex than the prior techniques, the reconstructed image is not exact.

Accordingly, U.S. patent application Ser. No. 09/162,303 entitled ADAPTIVE MASK BOUNDARY CORRECTION IN A CONE BEAM IMAGING SYSTEM, filed Sep. 28, 1998, now U.S. Pat. No. 6,084,937 issued Jul. 4, 2000, and also incorporated herein by reference, describes a technique for computing 2D correction data which, when combined with the ramp filtered 2D approximation data sets, yields an exact image reconstruction. The 2D correction data basically comprises a point spread function representative of image reconstruction processing for each point on the detector which intersects the boundary of the data-combination mask. However, the techniques disclosed therein require circle scan paths near the top and bottom edges of the ROI when only an ROI is to be imaged. It would be desirable to provide such a simplified image reconstruction processing without the requirement of circle scan paths near the top and bottom edges of the ROI.

The present inventor's allowed U.S. patent application Ser. No. 09/343,770 entitled EXACT REGION OF INTEREST CONE BEAM IMAGING WITHOUT CIRCLE SCANS, filed Jun. 30, 1999, incorporated by reference herein, improved upon the invention described in the forenoted U.S. Pat. No. 5,504,792, by providing an exact image reconstruction of an ROI in an object without the requirement that the source scan path have top and bottom circle scan paths near the top and bottom edges of the ROI. Furthermore, the improvement is applicable to both of the Radon space and detector driven types of image reconstruction processing. As described in this U.S. patent application Ser. No. 09/343,770, and consistent with the techniques described in the above noted U.S. Pat. Nos. 5,881,123 and 5,504,792, when calculating the derivative data, the length of the line segments L formed in the acquired cone beam data (along which integral data is to be developed) are determined by the boundaries of the data-combination mask. Exact image reconstruction processing for source positions which are "internal" to the top and bottom edges of the ROI can use the simplified ramp filtering with 2D correction data technique of the forenoted U.S. patent application Ser. No. 09/162,303. However, when processing cone beam data acquired at source positions near the top or bottom edges of the ROI, the line segments L are divided into two groups, where in one of the groups the line segments L have one of their end points determined by a horizontal line of the mask (in a preferred embodiment this horizontal line is the x-axis of the mask), instead of having both of the endpoints determined by the outer boundaries of the mask. When processing along the line segments L in this one group, acquired cone beam data which resides along lines L on the other side of the horizontal axis of the mask are not used. Thereafter, integral data is calculated for the line segments L having their endpoints limited by the horizontal axis in the mask, and the data is further processed so as to develop contributions to a 3D image reconstruction of the ROI in the object.

Figure 1A:
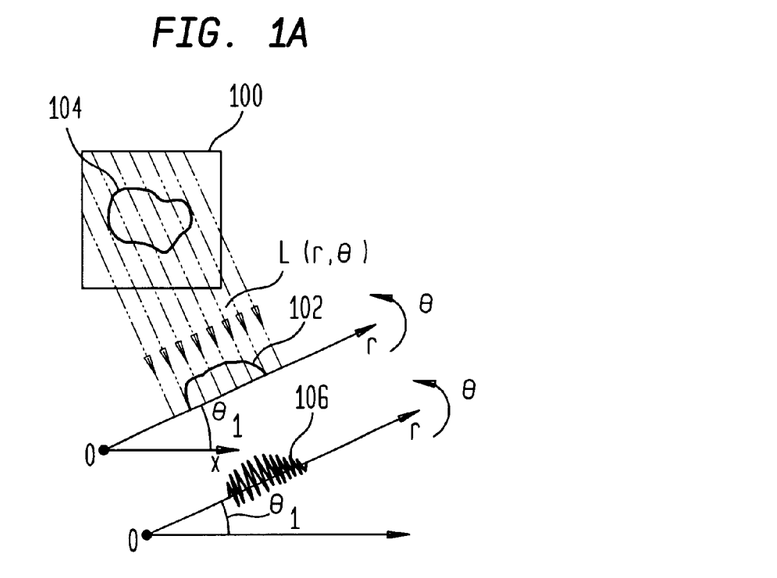
FIGS. 1A and 1B, previously described, illustrate a prior art 3D backprojection approach for reconstructing an image using the apparatus of FIG. 2.
Figure 1B:
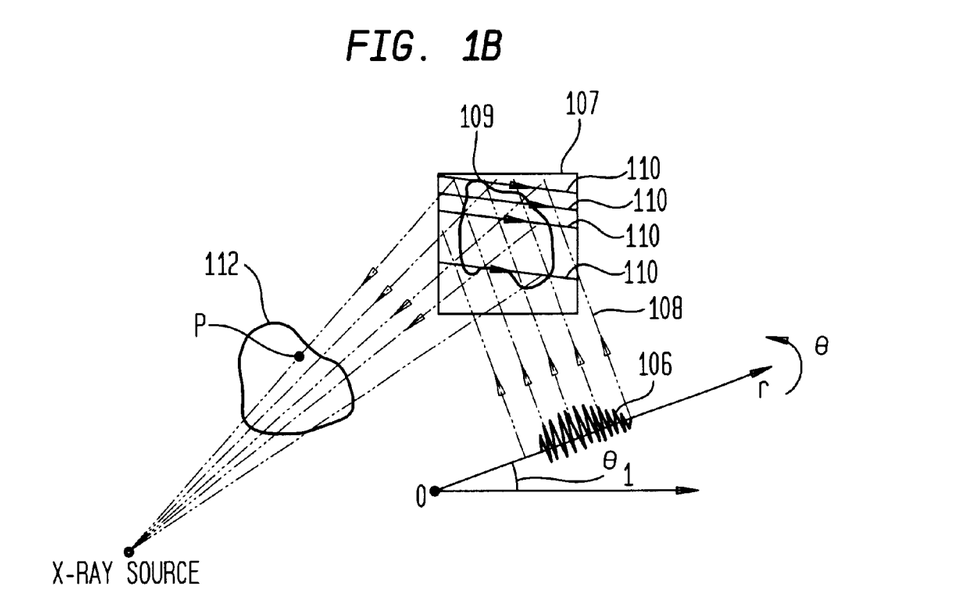
Figure 3A:
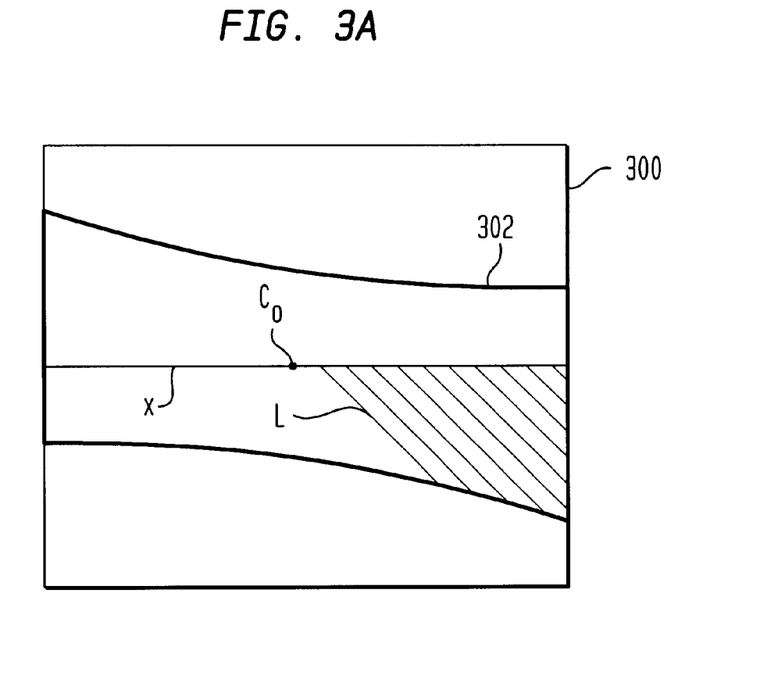
FIGS. 3A and 3B illustrate masking of lines formed in the sets of cone beam data acquired near the top edge of an ROI in an object, for use reconstructing an image in accordance with a prior art technique.
Figure 3B:
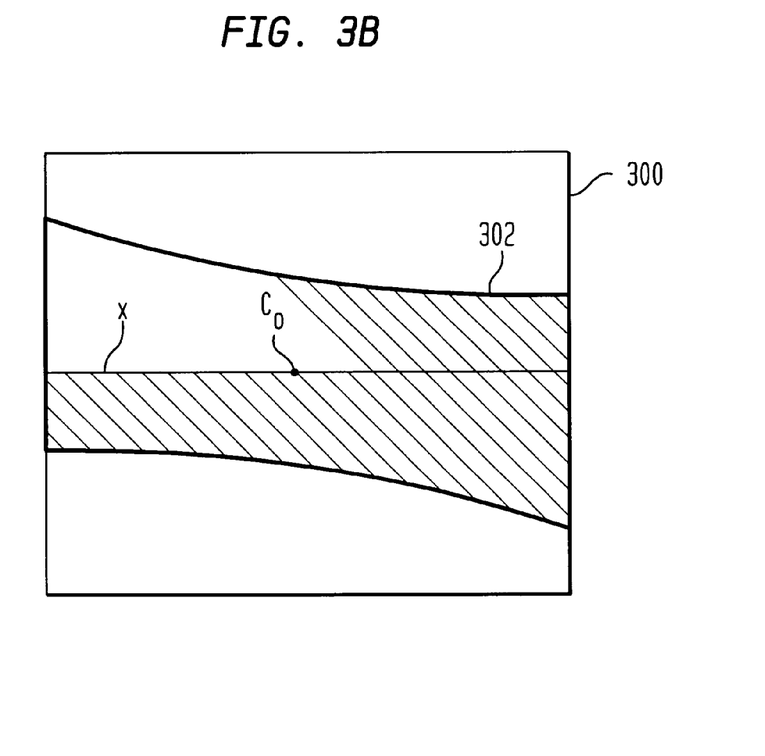

More specifically, when processing cone beam data acquired at source positions near the top or bottom edges of the ROI, the Filtered Backprojection (FBP) image reconstruction technique described in the forenoted U.S. patent application Ser. No. 09/343,770 can be used. FBP image reconstruction consists of two different kinds of processing: the first kind is 2-dimensional (2D) and the second kind is 3-dimensional (3D). In the 2D step each cone beam projection image is processed in a 2D space, and in the 3D step the processed 2D images are backprojected into a 3D object space. As shown in FIGS. 1A and 1B, the 2D step consists of the following 4 FBP image reconstruction sub-steps for processing the cone beam data acquired at each of a plurality of the source positions ($S_i$) along the scan path:

1. Compute a 1D projection (i.e., a line integral) of the cone beam image acquired on a detector plane 100, at each of a plurality of angles θ. This step is illustrated in FIG. 1A for a given angle $θ_1$ of a plurality of angles $θ_1$. A 1D projection 102 is shown at coordinates r, $θ_1$ comprising the integrated values of the cone beam image 104 on detector plane 100 along a plurality of parallel lines L(r, $θ_1$) that are normal to angle $θ_1$, each line L being at an incremental distance r from an origin O. As shown and described below in conjunction with FIGS. 3A and 3B illustrating processing of cone beam data acquired near the top edge of the ROI, the lengths of the lines L will be limited using the masking techniques of the forenoted U.S. patent application Ser. No. 09/343,770. Generally, if the detector plane 100 comprises an N by N array of pixels, then the number of angles θ is typically given by πN/2.

2. Filter (differentiate) each 1D projection 102 in accordance with a d/dr filter, resulting in a new set of values at each of the r, θ coordinates, such as shown by the derivative projection 106 for the angle $θ_1$, shown in FIG. 1A. Note, the sum (integration) of the resulting values at these r, θ coordinates yield a quantity proportional to the Radon derivative for an integration plane Q(r, θ), as described above for Radon space driven image reconstruction processing.

3. As illustrated by FIG. 1B, backproject the derivative projection 106 from each angle θ into a 2D object space 107 (which coincides with the detector plane 100). Lines 108 are representative of this backprojection, and spread the value from each r coordinate into 2D space 107 in a direction normal to each θ, thereby developing contributions to a backprojection image 109. Note, 2D object space 107 has a size corresponding to a virtual detector which is enlarged (compared with detector having a height corresponding to the pitch of the scan path), so as to cover the entire ROI in the object. This enlargement is required because the calculated Radon data affects the reconstruction of the entire Q plane, and not just the partial plane represented by the data combination mask.

4. Perform a 1D d/dt filtering of the backprojection image formed in 2D space 107 by step 3. The 1D filtering is performed in the direction of the scan path, i.e., along lines 110, where t points in the direction of the projection of a line drawn tangent to the scan path.

As shown in FIG. 1B, the 3D step comprises performing a weighted 3D backprojection of the resulting data from 2D space 107 (i.e., from each pixel in the detector) onto a plurality of sample points P in a 3D object volume 112. The density assigned to each point P is weighted by the inverse of the square of the distance between the sample point and the location of the x-ray.

Although this technique allows exact image reconstruction without the requirement of a circle scan path near the top and bottom edges of the ROI in the object, the 4-substeps of 2D processing as described above, is relatively complex and time consuming, since it is required to be repeated for each angle θ.

It would be desirable to provide a simplified (i.e., less complex and time consuming) image reconstruction processing, such as that described in the forenoted U.S. Pat. No. 5,881,123, which does not require the use of circle scans near the top and bottom edges of the object being imaged.

SUMMARY OF THE INVENTION

A scanning and data acquisition method and apparatus for three dimensional (3D) computerized tomography (CT) imaging of an ROI in an object, wherein a reconstructed image is develop by calculating reconstruction data along a plurality of line segments L formed in cone beam data acquired on a detector at a plurality of source positions about the ROI. The endpoints of the line segments L formed in the cone beam data acquired at each of the source positions is determined by a data combination mask which is applied to the cone beam data. At source positions near the top and bottom of the ROI, the mask is divided into separate portions using at least a horizontal line therein, each portion having a corresponding set of line segments L formed therein. The reconstruction data is calculated by performing a plurality of one-dimensional (1D) convolving operations of the masked projection data along a respective set of the line segments L, the 1D convolving operation for each set of the line segments L developing an additive contribution to a new projection image. Finally, the new projection image is backprojected into a 3D space, thereby reconstructing a 3D image of the ROI in the object.

Thus, in accordance with the principles of the present invention, the most time-consuming tasks in backprojection ROI spiral scan cone beam CT, i.e., the 2D projection and 2D backprojection on the detector plane for the views near the two ends of the spiral, are combined into 1D Hibert Transforms, thereby tremendously simplifying the image reconstruction operation.

DETAILED DESCRIPTION OF THE INVENTION

Figure 2:
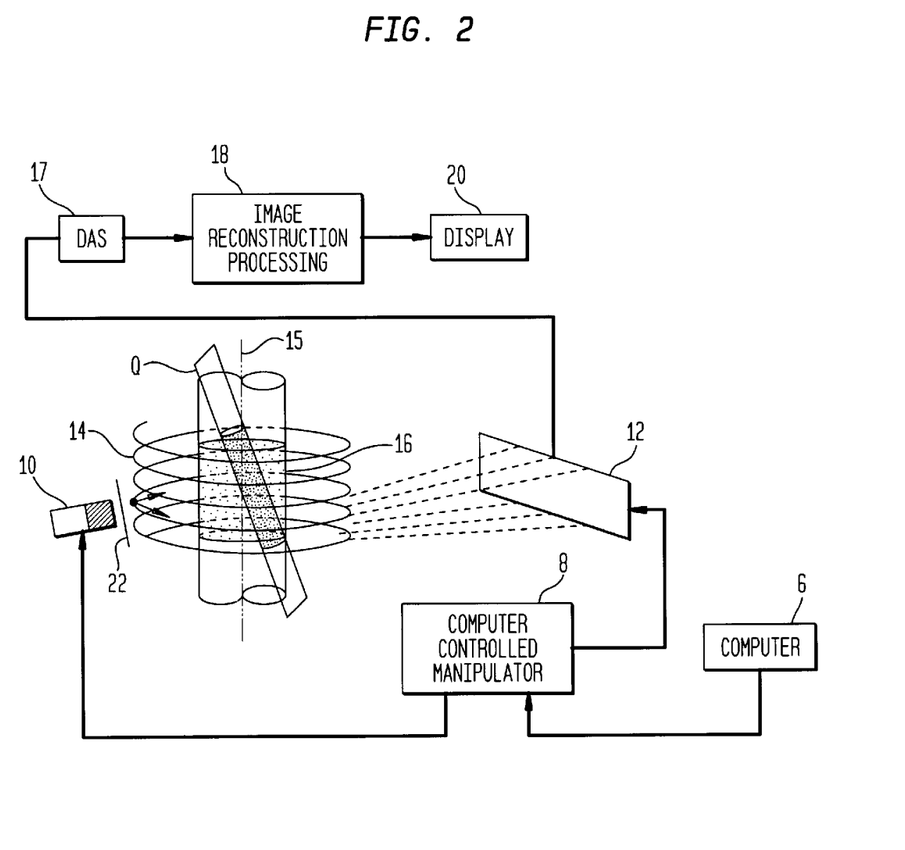
FIG. 2 illustrates a 3D CT imaging apparatus useful for acquiring and processing cone beam data in accordance with the principles of the present invention.

FIG. 2 illustrates a cone beam 3D CT imaging apparatus useful for acquiring and processing acquired cone beam data in accordance with the principles of the present invention. The illustrated imaging apparatus is constructed and operates substantially in accordance with the same principles described in the forenoted U.S. Pat. No. 5,257,183 and uses a masking image reconstruction technique such as described in the forenoted U.S. patent application Ser. No. 09/343,770, already incorporated herein by reference. Furthermore, image reconstruction processing in accordance with the present invention is accomplished in conjunction with a radiation blocking shutter for blocking radiation exposure to a portion of the object at source positions near the top and bottom edges of the ROI, as will be more specifically described below.

As shown in FIG. 2, a computer controlled manipulator 8, in response to control signals from an appropriately programmed computer 6, cause a source 10 of a cone or pyramid shaped beam of energy (such as x-rays) and a two-dimensional pixelated detector array 12 to cooperate (scan) at a plurality of discreet, sequentially occurring adjacent source positions, along a pre-defined source scanning path. In the illustrated embodiment the scanning path is shown as a spiral scan path 14 centered on a predetermined axis 15 of an object 16, and which proceeds in a counter-clockwise direction and spiraling upward. Other types of scan paths that encircle and traverse object 16 can also be used, however, a scan path 14 exhibiting a high degree of symmetry in its parallel projection is preferred.

The only height requirement on the detector is that it should be more than the distance between adjacent turns of a cone beam projection of the spiral scan path 14 onto the detector 12. As described in the forenoted U.S. patent application Ser. No. 09/343,770, when only a "region of interest" (ROI, shown as the shaded area of object 16) is to be imaged, providing top and bottom scan path circles at the top and bottom ends, respectively, of the ROI, are not necessary. Thus, a simple continuous spiral scan path 14 that traverses the length of the ROI is all that is needed.

As a result of the source/detector cooperation under control of computer 6 and manipulator 8, at each of the source positions, beams of x-ray energy pass through the field of view of the imaging apparatus, are selectively attenuated by varying energy absorbing densities inside object 16, and a set of cone beam data corresponding to the sensed x-ray energy falling on the elements (pixels) of detector 12 are developed. The sets of cone beam data are then supplied to a data acquisition system (DAS) 17 which, like the previously described portions of FIG. 1, may operate in a fashion well known to those of ordinary skill in this technology for digitizing and storing of the acquired cone beam data.

As described in the present inventor's forenoted U.S. Pat. No. 5,257,183, image reconstruction processing 18 begins by calculating derivative data from the acquired cone beam data, such data being calculated for those portions of integration planes Q which intersect both the scan path and the ROI. One such Q-plane is shown in FIG. 2. In the forenoted U.S. Pat. No. 5,257,183, Radon space driven conversion of the derivative data is used to develop an image reconstruction of object 16 on a display 20. However, image reconstruction processing 18 of the present invention uses a detector data driven technique, such as the simplified 3D backprojection technique described in the forenoted U.S. Pat. No. 5,881,123.

In accordance with the principles of the present invention, and simplified image reconstruction processing is provided, which processing does not require that the imaging apparatus provide circle scan paths near the top and bottoms of the ROI.

Furthermore, a radiation blocking shutter 22 is also provided in the FIG. 2 apparatus and selectively operated so as to reduce the radiation dose directed toward the object being imaged during that portion of the scan path which is proximate the top and bottom portions of the ROL More specifically, as will be described below, there are source positions proximate the top and bottom of the ROI where the cone beam data acquired on the top and bottom half of the detector, respectively, will not be used. Accordingly, at these source positions, shutter 22 is activated to block radiation directed to the portion of the detector that will not be used.

In order to more fully understand the principles of the present invention, some review of the previously noted U.S. patent application Ser. No. 09/343,770 will be provided. As was noted above, this technique for ROI imaging does not have the requirement that the imaging apparatus provide circle scans even with the top and bottom ends of the ROI. This is accomplished by processing the acquired cone beam data using a "local 2 ROI" approach, as was first described in the present inventor's U.S. patent application Ser. No. 09/052,415 entitled PRACTICAL CONE BEAM IMAGE RECONSTRUCTION USING LOCAL REGIONS-OF-INTEREST, filed Mar. 31, 1998, incorporated herein by reference, wherein specific sub-sets of Radon space data are developed. Each of the subsets of Radon space data is targeted for reconstructing a corresponding sub-section or "local" portion of a 2D ROI. Each local ROI is a 2D parallel projection of the ROI in the object on an individual one of the plurality of vertically oriented coaxial φ-planes that partition the Radon space. Due to the nature of a parallel projection, the upper and lower bounds of the local 2D ROI projection images do not suffer data corruption from x-rays emitted from the source which pass through areas outside the bounds of the local ROI. When a sufficient number of these local 2D ROI projection images are developed over 180 degrees (the sufficiency being determined by the desired resolution of the final image reconstruction), they are processed, using Radon inversion techniques, for directly developing contributions to the final image reconstruction, thereby obviating the requirement to provide circle scans at the top and bottom ends of the ROI.

In the forenoted U.S. patent application Ser. No. 09/343,770 these image reconstruction techniques are further simplified and extended for use in a Filtered Backprojection (FBP) image reconstruction arrangement.

The FBP image reconstruction technique was previously described in conjunction with FIGS. 1A and 1B.

When reconstructing an image using data acquired from source positions which are "internal" to the top and bottom 2π angular range of the scan path about the ROI, the simplified ramp filtering/data-combination masking technique known from the forenoted U.S. patent application Ser. No. 09/162,303 can be used. However, when reconstructing an image from data acquired at source positions which are near (i.e., "within") the top and bottom 2π angular range of the scan path about the ROI, if there are no circle scans, in accordance with the teachings of the forenoted prior art U.S. patent application Ser. No. 09/343,770, the techniques shown in FIGS. 3A and 3B (and processed according to the forenoted FBP image reconstruction sub-steps (1)–(3) ) could be used. However, the 2D projections and 2D backprojections for each θ onto the detector plane for the views near the two ends of the spiral, is a very time-consuming task.

The present invention simplifies this task

Figure 4:
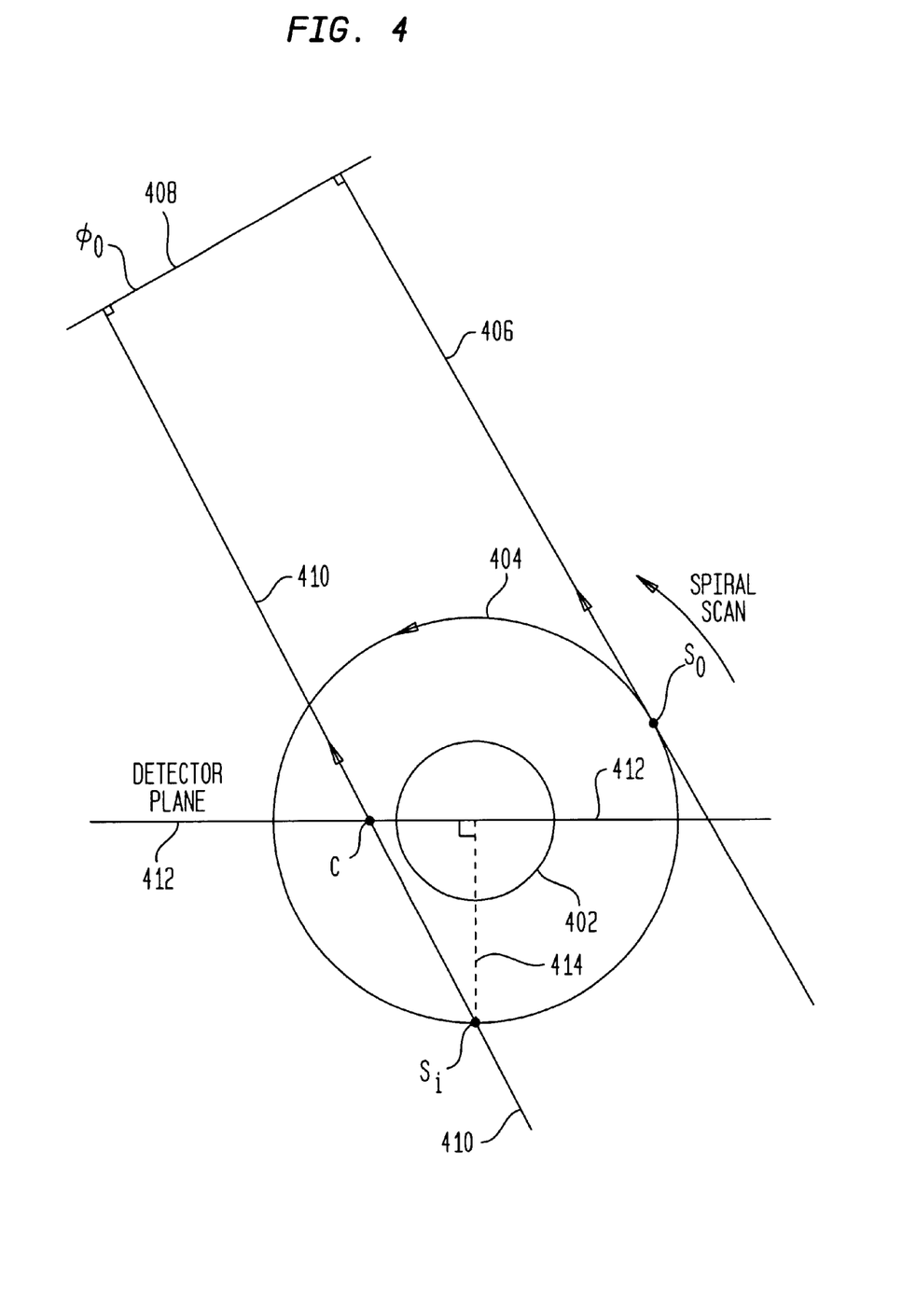
FIG. 4 illustrates a top view of a portion of the image reconstruction geometry used to determine the point $C_0$ in the masks shown in FIGS. 3, 7 and 9 to 11.

More specifically, as shown in FIGS. 3A and 3B, in a set of cone beam data 300 acquired at a given source position $S_i$, a point $C_0$ is marked on the x-axis of the detector. The technique for marling the point $C_0$ is described in detail in the forenoted U.S. patent application Ser. No. 09/343,770, and will be described more briefly below in conjunction with FIG. 4. Next, an appropriate data combination mask 302 is applied to the cone beam data, and a plurality of lines L are formed in each set 300 of the acquired cone beam data in accordance with the forenoted sub-step (1) of FIG. 1A. As previously noted, the endpoints (and hence the length) of the line segments L are determined by the outer boundaries of the data combination mask for all source positions that are "internal" of the top and bottom 2π angular range in the scan path that are near the top and bottom edges, respectively, of the ROI. However, at source positions which are "within" the top and bottom 2π angular ranges (i.e., the outermost or first turns) in the scan path, the endpoints for at least some of the line segments drawn in the acquired cone beam data are determined by one boundary and the horizontal axis of the data combination mask, as shown in FIGS. 3A and 3B. That is, all line segments L which cross the horizontal axis to one side of a point $C_0$ (which point is determined as shown in FIG. 4), have their endpoints determined by one of the upper or lower boundaries of the mask and its horizontal (i.e., x) axis, and all of those line segments crossing the horizontal axis to the other side of $C_0$, are either not used, or are determined by outer boundaries of the data combination mask. (Note, in the illustrated embodiment the x-axis of the data combination mask is coincident with the x-axis of the detector, but such coincidence is not required.)

The following analysis, in conjunction with FIG. 4, describes how to determine the point $C_0$ in the data acquired at any source position $S_i$, scanning towards an end source position $S_0$. FIG. 4 illustrates a top view of a portion of the image reconstruction geometry, wherein a circle 402 is representative of the object and a circle 404 is representative of the spiral path traversed by the x-ray source S (shown as 10 in FIG. 2). The ending source position $S_0$ is marked on scan path circle 404. As previously described, in order to provide an exact image reconstruction and avoid image artifacts, a parallel projection of the scan path must, at a minimum, begin and end outside of the local ROI of the object. Accordingly, a line 406 is drawn starting from source position $S_0$ so as to be tangential to circle 404 (i.e., touching the outside edge of scan path 14). The Radon space φ-plane which forms an orthogonal intersection with line 406 defines the Radon space $φ_0$-plane, which is labeled 408.

Then, assuming an anti-clockwise rotation of the source S, mark a source position $S_i$ on scan path circle 404. Next, one draws a line 410 which passes through source position $S_i$ and is parallel with line 406, and therefore also bears an orthogonal relationship to the Radon space $φ_0$-plane 408. Then, $C_0$ is defined as that point on the x-axis in the detector plane that acquires the cone beam data at source position $S_i$, which is intersected by line 410. (Note, the detector plane that acquired the cone beam data at source position $S_i$, i.e., detector plane 412, is determined by its orthogonal relationship to a line 414, which is drawn from source position $S_i$ to the center of object circle 402.) This $C_0$ is used, as noted above, to group the line segments L formed in the cone beam data during image reconstruction processing, in accordance with the manner of their length limitation. In this manner, the location of $C_0$ for all of the source positions S can be determined. (The anti-clockwise rotation assumed in the above analysis can be easily modified for the opposite sense of source rotation.)

As described above, it is clear that the line integrals are not computed between fixed boundaries. Accordingly, the line integrals are not in the form of the projections of a function, and therefore the 2D step of the reconstruction processing (the forenoted FBP image reconstruction sub-steps (1)–(4)) cannot be simplified in the same way as was described in the forenoted U.S. Pat. No. 5,881,123.

The present invention simplifies the 2D step into 1D operations for the data acquired at the views near the two ends of the spiral.

In accordance with the principles of the present invention, these most time-consuming tasks are combined into convolving operations, and more specifically, 1D Hilbert Transform steps, thereby tremendously simplifying this portion of the image reconstruction processing.

In an effort to explain the theory behind the present invention, it is noted that the resulting 2D image 109 of FIG. 1B, after processing the cone beam data according to 4 FBP image reconstruction sub-steps described in the forenoted U.S. patent application Ser. No. 09/343,770, can be written as:

$$Y = D_i \{ \int d\theta [B(\theta) D_r(\theta) P(\theta)] \} M(X) \tag{1}$$

where

X=cone beam image

M=masking

P(θ)=projection in the direction θ

$D_r(\theta)$=differentiation w.r.t. the variable r for the projection at angle θ

B(θ)=backprojection in the direction θ

$D_t$=differentiation (spatial) in the projected scan path direction t

The projection and backprojection operations in Equation (1) are carried out for all θ in the angular range [$\theta_t$-π/2, $\theta_t$+π/2], where $\theta_t$ is the angular displacement (from the x axis) of the direction t, which direction is the projection of the current scan path tangent on the detector. The angular range [$\theta_t$-π/2, $\theta_t$+π/2] ensures that the product of the derivative d/dt with d/dr has the same sign for all the angles within the range; otherwise the signs of the product at different angles will be inconsistent.

For views in the "interior" of the spiral, the projection operation (1) is applied to the entire masked cone beam image M(X). It was shown in the forenoted U.S. Pat. No. 5,881,123 that under such circumstances, the 2D step (Equation (1)) can be greatly simplified, and the image Y (109 of FIG. 3B) can be written as:

$$Y = R_t M(X) + C \qquad (2)$$

where $R_t$ is the 1D ramp filtering operation in the direction t. The term C in Equation (2) is a 2D "correction" term obtained by convolving all the pixels intersecting the mask boundary with a space-variant 2D detector pixel point spread function representative of the effect of the image reconstruction processing upon that point.

For the views near the two ends of the spiral, however, as shown in FIGS. 3A and 3B, and described in the forenoted U.S. patent application Ser. No. 09/343,770, the projection operation (1) is applied to only part of the masked cone beam image M(X). Accordingly, the 2D reconstruction processing step cannot be simplified in the same way as was described in the forenoted U.S. Pat. No. 5,881,123.

As noted above, the present invention simplifies the 2D step (Equation (1)) into a series of 1D operations for the views near the two ends of the spiral.

As proof for the invention, it will first be shown that FBP image reconstruction sub-steps (1) through (3) of the above noted 4 FBP image reconstruction sub-steps can be combined into a 1D convolution step. As mentioned above, FBP image reconstruction sub-steps (1) through (3) are carried out for θ in the angular range [$\theta_t$-π/2, $\theta_t$+π/2], where $\theta_t$ is the angular displacement of the direction t which is the projection of the current scan path tangent on the detector. At each angle the direction of the variable r determines the direction of the derivative operation d/dr in sub-step (2) (thus the derivative operations in θ and θ+π will proceed in opposite directions). The angular range [$\theta_t$-π/2, $\theta_t$+π/2] ensures that the product of the derivative d/dt with d/dr has the same sign for all the angles within the range; otherwise the signs of the product at different angles will be inconsistent. To stress the importance of this angular range, we state it as a proposition:

Proposition 1.

The direction of the derivative operation d/dr in sub-step (2) follows the direction of the variable r in the angular range [$\theta_t$-π/2, $\theta_t$+π/2].

The 1D simplification of the 2D operations, as provided by the present invention, is based on the following analysis.

Theorem 1.

The combined operations of FBP image reconstruction sub-steps (1) through (3) in the angular range [$\theta_t$-π/2, $\theta_t$+π/2] is equivalent to the 1D Hilbert transform in the direction t.

Proof:

$$\{\int d\theta[B(\theta)D_r(\theta)P(\theta)]\}(f(\rho,\alpha)) = \int d\theta \int dk(ik)F(k,\theta)\exp(ik\rho \cos(\theta-\alpha))) = \int\int d\theta dk|k|H(k)F(k,\theta)\exp(ik\rho \cos(\theta-\alpha)) \qquad (3)$$

where r=ρcos(θ-α)  H(k)=i sgn(k•t).

Figure 5:
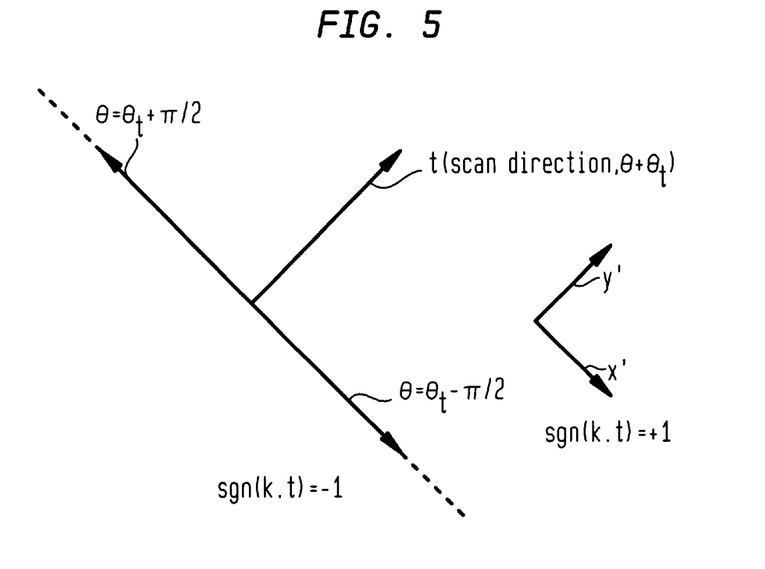
FIG. 5 illustrates geometry usefull for understanding how the combined operations of FBP image reconstruction sub-steps (1)–(3) of FIGS. 1A and 1B are equivalent to a 1D Hibert transform in the direction t.

FIG. 5 spatially illustrates where the term "sgn(k•t)", as used in equation (3), is +1 or −1.

Thus $$\{\int d\theta[B(\theta)(d/dr)P(\theta)]\}(f(\rho,\alpha)) = h*f$$

where $$h = \text{Fourier transform of } H(k) \qquad (4)$$
$$= g(v)\delta(u)$$

where (u, v), shown in FIG. 5, is the (x, y) coordinate system rotated such that the y' axis coincides with the direction t. Accordingly:

$$u = x \cos(\theta_t - \pi/2) + y \sin(\theta_t - \pi/2)$$
$$v = -x \sin(\theta_t - \pi/2) + y \cos(\theta_t - \pi/2)$$

The 1D function g(v)= is the Fourier transform of the function i sgn(k). It's functional form is given by:

$$g(v) = -1/(\pi v)$$

and is known as the Hilbert transform (well known to those skilled in CT image reconstruction technology, and described in detail, for example by R. N. Bracewell, in "The Fourier Transform and Its Applications", 1978, McGraw-Hill, p.267).

Thus the result of FBP image reconstruction sub-steps (1) through (3) on the function f is the convolution of f with the point spread function (PSF) h. Even though h is a 2D function, Equation (4) indicates that it is zero everywhere except on the line θ=$\theta_t$. Thus h is essentially a 1D function along the line θ=$\theta_t$. The 1D function can be written as h(x,y;x',y';$\theta_t$) to represent the value produced at a field point (x,y) as a result of applying the FBP image reconstruction sub-steps (1) through (3) on a source point (x',y') which has a density value of unity.

Theorem 2.

The combined operations of FBP image reconstruction sub-steps (1) through (3) in the angular range [$\theta_1$, $\theta_2$], where $\theta_1 \in [\theta_t-\pi/2, \theta_t+\pi/2]$ and $\theta_2 \in [\theta_t-\pi/2, \theta_t+\pi/2]$, is equivalent to the sum of two 1D Hilbert transforms: (½)h(x,y;x',y'; $\theta_2$-π/2)+(½)h(x,y;x',y'; $\theta_1$+π/2).

Figure 6A:
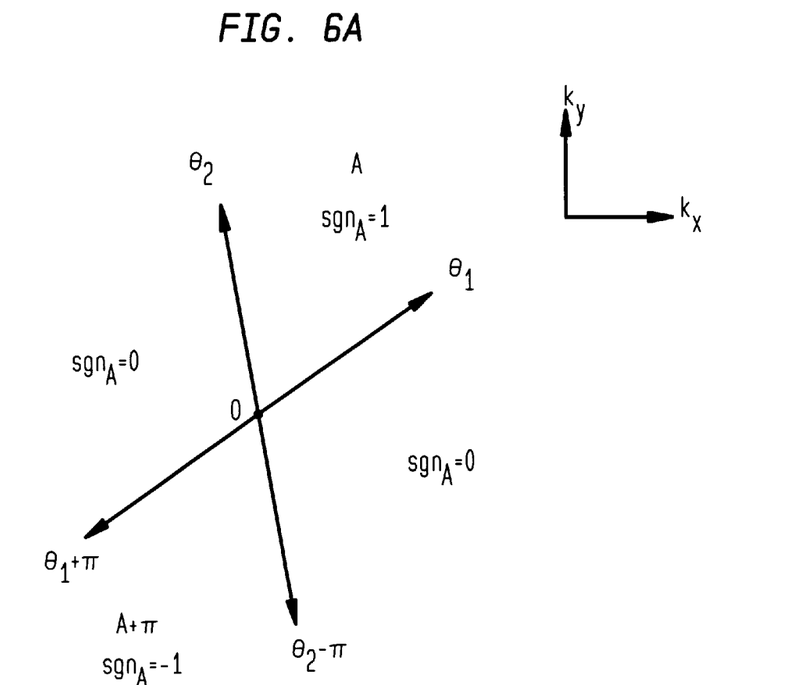
FIGS. 6A, 6B and 6C illustrate a geometry useful for understanding how the combined operations of FBP image reconstruction sub-steps (1)–(3) within a given angular range are equivalent to the sum of two 1D Hilbert transforms.
Figure 6B:
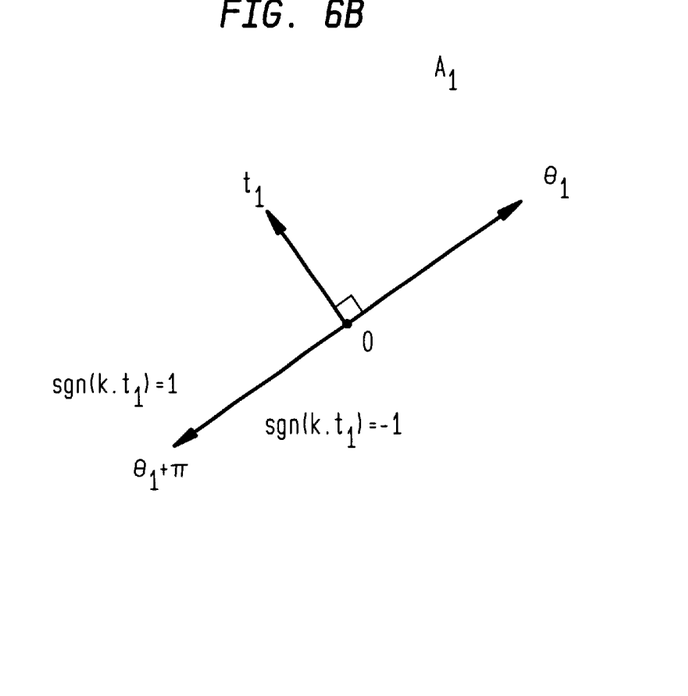
Figure 6C:
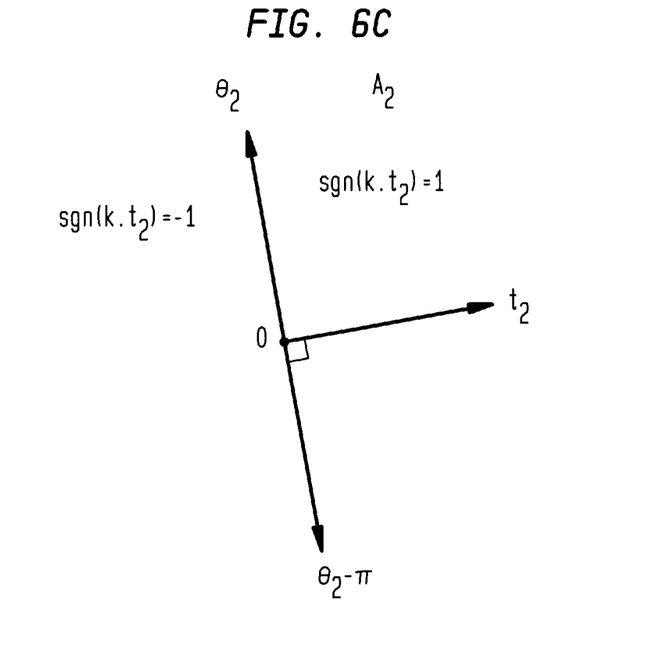

Proof of Theorem 2 is now provided, in conjunction with the illustrations in FIGS. 6A, 6B and 6C.

Employing a procedure similar to the one leading to Equation (3), we have $$\{\int_a d\theta[B(\theta)D_r(\theta)P(\theta)]\}(f(\rho,\alpha)) = H_A * f \qquad (5)$$

where $$h_A = \text{Fourier transform of } (i\ sgn_A(k))$$

where, as shown in FIG. 6A $$sgn_A(k) = 1 \qquad k \in A$$
$$= -1 \qquad k \in A + \pi$$
$$= 0 \qquad \text{Otherwise}$$

Considering two angular ranges $A_1$ and $A_2$, shown in FIGS. 6B and 6C, respectively:

$A_1=[\theta_1,\theta_1+\pi]$, $t_1$=direction vector at $\theta=\theta_1+\pi/2$, $h_1=FT[i\ sgn(k\cdot t_1)]$ $A_2=[\theta_2-\pi,\theta_2]$, $t_2$=direction vector at $\theta=\theta_2-\pi/2$, $h_2=FT[i\ sgn(k\cdot t_2)]$ From inspection of FIGS. 6A–6C, is is clear that:

$sgn_A(k)=(\tfrac{1}{2})[sgn(k\cdot t1)+sgn(k\cdot t_2)]$ (i.e., FIG. 6A=½(FIG. 6B+FIG. 6C)

Thus $h_A=(\tfrac{1}{2})[h_1+h_2]$

Applying Threorem 1 to $A_1$ and $A_2$ yields the desired result.

Next, in accordance with the principles of the invention, Theorems 1 and 2 are applied to simplify the know prior image reconstruction processing for cone beam data which is acquired near the edges of the ROI, and without circle scans.

Without loss of generality, assume the spiral scanning motion is right-handed with the spiral axis pointing in the +y direction; the analysis can easily be modified for other scanning configurations. Thus the direction t, which is the projection of the current scan path tangent onto the detector, points in the direction $\theta_t\ [0,\pi/2]$.

We first consider the view angular range $[\pi, 2\pi]$ measured from the spiral end, with the corresponding limits for the projection operation being as shown in FIG. 3B. Considering a source point $P=(x',y')$, there are generally two possibilities:

Case 1.
Where y'<0 (i.e., all source points P are below the x-axis in the mask, i.e., are in its bottom half.)

Line integrals are computed on all line segments through P. The angular range of the projection and backprojection operations is therefore $\pi$. Application of Theorem 1 yields the result:

PSF at $P=h(x,y;x',y';\theta_t)$

I.e., the result is a 1D Hilbert transformation in direction t for each point P on the detector which is below the x-axis.

Figure 7:
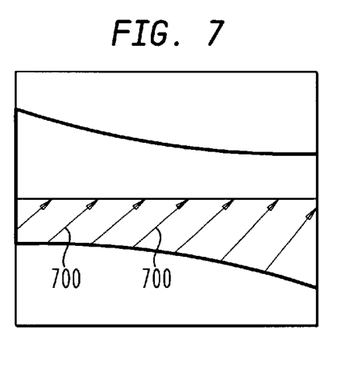
FIG. 7 illustrates a portion of image reconstruction processing in accordance with the invention for a source point P which is below the x-axis in the data-combination mask.

FIG. 7 illustrates the taking of these 1D Hilbert transformations along a plurality of parallel line segments 700 drawn in the bottom half of the masked data.

Note, the results of these transformations, as well as the transformations noted below, are spread out over a virtual detector which is enlarged (compared with a detector having a height corresponding to the pitch of the scan path), so as to cover the entire ROI in the object. As previously noted, this enlargement is required because the calculated data affects the reconstruction of the entire Q plane, and not just the partial plane represented by the data combination mask.

Case 2. Where Y'>0

Figure 8A:
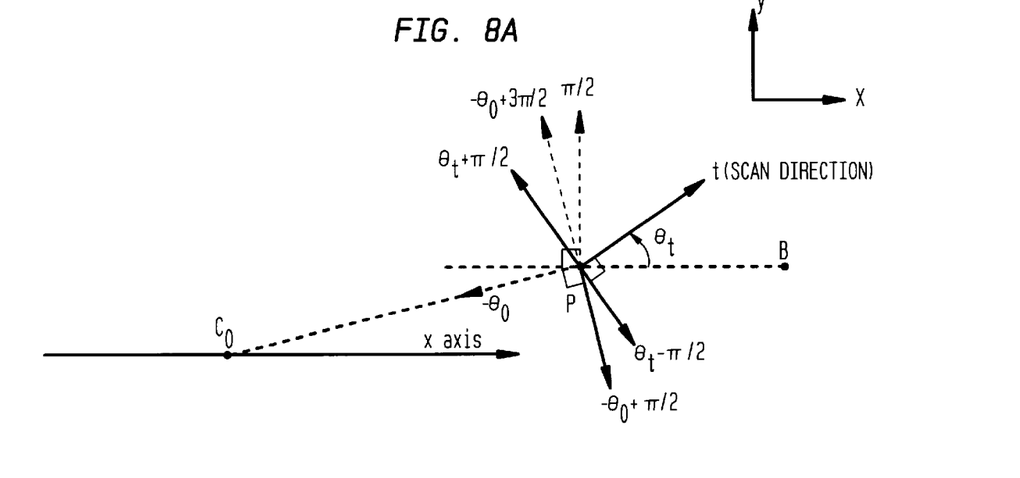
FIGS. 8A and 8B illustrate geometry useful for understanding how the image reconstruction processing varies depending upon where the source point P resides on the top half of the data-combination mask.
Figure 8B:
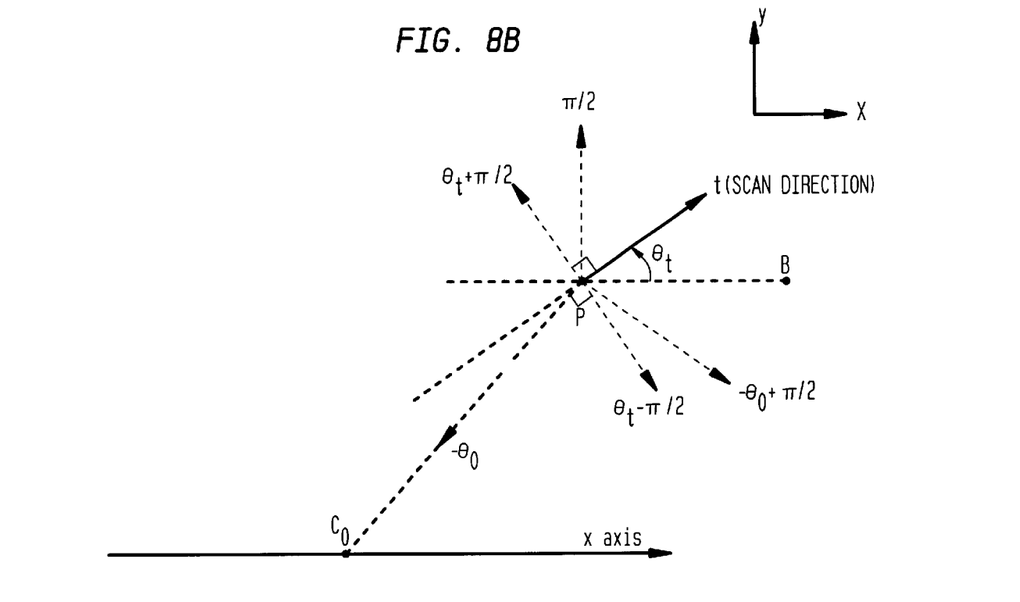

Let $C_0$ be the point on the x axis which divides the x axis into data-combination limited and ROI-edge limited portions, as described in the forenoted U.S. Ser. No. 09/343,770. For the assumed scanning motion, it can be shown that the portion to the right of $C_0$ is data-combination limited, and that the portion to the left of $C_0$ is ROI-edge limited. Referring now to FIGS. 8A and 8B, illustrating a masked set of acquired cone beam data, let a point $B=(x_b,y')$ be a point on a horizontal line through point P such that $X_b>x'$, i.e. B is on the right hand side of P. Consider all the line integrals through the point P. These line integrals occur in the angular range bound by the line segment $PC_0$ anti-clockwise through the line segment PB. Although not shown in FIGS. 8A and 8B, it is understood that the integration line segments are limited by the top and bottom boundaries of the data-combination mask as described in the forenoted U.S. Ser. No. 09/343,770. Let $-\theta_0(\theta_0>0)$ be the angular displacement of the line segment $PC_0$ from the x axis. Image reconstruction processing for line segments in this range of angular displacement resolves into one of two sub-cases.

Sub-Case 2.1, where $\theta_t-\pi/2>-\theta_0+\pi/2$ (i.e., a line drawn in the t direction crosses the x-axis to the right of $C_0$, as shown in FIG. 8A,) Consider the line integral on the line segment PB. Depending on the direction of integration, the line integral can be considered as belonging to either the projection at $\theta=\pi/2$ or the projection at $=-\pi/2$. Since Proposition 1 requires that the projection/backprojection angle should be inside the angular range $[\theta_t-\pi/2, \theta_t+\pi/2]$, $\theta=/2$ is the projection/backprojection angle. Following this line of argument it can be shown that the projection/backprojection angular range corresponding to all the line integrals in the angular range bound by the line segment $PC_0$ anti-clockwise through the line segment PB is $A1\cup A_2$, where $A_1=[\theta_t\pi/2, \pi/2]\subset[\theta_t-\pi/2, \theta_t+\pi/2]$ and $A_2=[\theta_0+3\pi/2, \theta_t+\pi/2]$. Application of Theorem 2 to $A_1$ yields the result:

PSF at P (due to $A_1$)=(½)h(x,y;x',y';0)+(½)h(x,y;x',y';$\theta_t$)     (6)

Application of Theorem 2 to $A_2$ yields the result:

PSF at P (due to $A_2$)=(½)h(x,y';x',y';$\theta_0$)+(½)h(x,y;x',y';$\theta_t$)     (7)

Combining the results (6) and (7) we have:

PSF at P=(½)h(x,y;x',y';+$\theta_0$)+(½)h(x,y;x',y';0)+h(x,y;x',y';$\theta_t$)

Figure 9A:
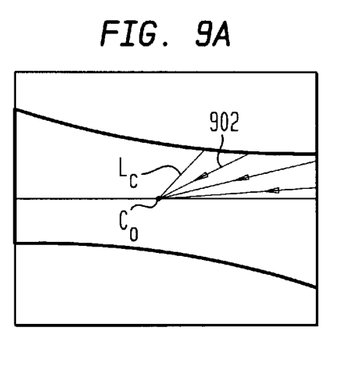
FIGS. 9A, 9B and 9C illustrate portions of image reconstruction processing in accordance with the invention for a source point P which is positioned in the data-combination mask according to the criteria of FIG. 8A.
Figure 9B:
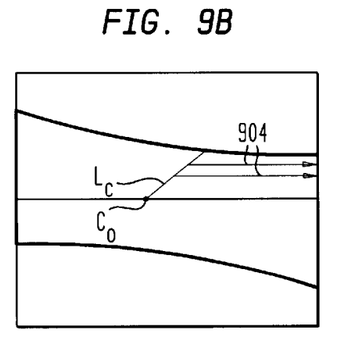
Figure 9C:
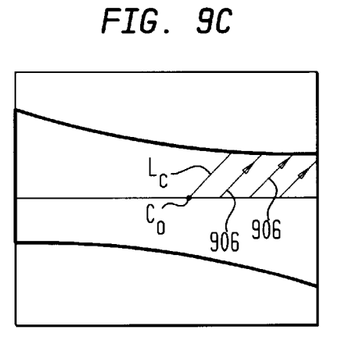

I.e., the result is the summation of three 1D Hilbert transformations for each point P which satisfies the criteria of this sub-case, as shown by lines 902, 904 and 906, respectively, in FIGS. 9A, 9B, and 9C.

Sub-Case 2.2. where $\theta_t-\pi/2<-\theta_0+\pi/2$ (i.e.a line drawn in the t direction crosses the x-axis to the left of $C_0$. as shown in FIG. 8B) Following the same reasoning used above, it can be shown that the projection/backprojection angular range corresponding to all the line integrals in the angular range bound by the line segment $PC_0$ anti-clockwise through the line segment PB is $[\pi/2,\theta_0+3\pi/2]\subset[\theta_t-/2, \theta_t+\pi/2]$. Application of Theorem 2 yields the result:

PSF at P=(½)h(x,y;x',y';-$\theta_0$+$\pi$)+(½)h(x,y;x',y'; 0)

Figure 10A:
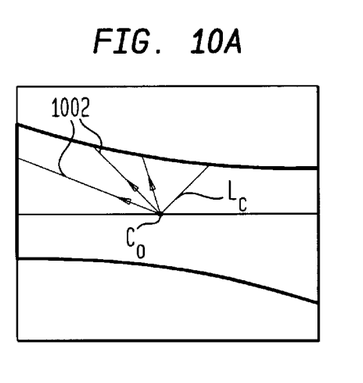
FIGS. 10A, and 10B illustrate portions of image reconstruction processing in accordance with the invention for a source point P which is positioned in the data-combination mask according to the criteria of FIG. 8B.
Figure 10B:
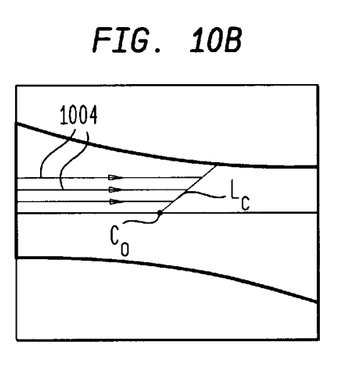

I.e., the result is the summation of two 1D Hilbert transformations for each point P which satisfies the criteria of this sub-case, each 1D transformation being in the direction as shown by lines 1002 and lines 1004, shown in FIGS. 10A and 10B, respectively.

Summarizing, for the view angular range $[\theta, 2\pi]$ measured from the end of the ROI, the above analysis has shown that applying FBP image reconstruction sub-steps (1) through (3) to any point on the detector, results in a number of essentially 1D PSF h, which, in accordance with the present invention, are additively combined for constructing the final backprojection image Y (109 of FIG. 1B), as follows:

For points in that portion of the image which is below the x axis (case 1):

1D Hilbert transform in the direction of the scan path [h(x,y;x',y';$\theta_t$)] (as shown by FIG. 7).

For points in that portion of the image which is above the x axis (case 2):

1D Hilbert transform in the x direction [h(x,y;x',y';0)] (as shown by the combination of FIGS. 9B and 10B).

Determine the point $C_0$ on the x axis where the current source position projects in the direction which projects the end source position onto the edge of the spiral cylinder.

1D Hilbert transform in the direction of the scan path the portion of the image above the x axis and to the right of the line (infinitely extended) through $C_0$ in the direction of the scan path fh(x,y;x',y';$\theta_t$)] (as shown by FIG. 9C).

1D Hilbert transform along each line intersecting the point $C_0$ [h (x,y;x',y';$-\theta_0$) or h(x,y;x',y';$\theta_0+\pi$)], respectively, as shown by the FIGS. 9A and 10A).

In a similar fashion one can work out the PSF for cone beam images acquired during the 0 to $\pi$ angular range of the scan path about the top end of the ROI, as follows:

Case 1. y'>0
  PSF at P=0
Case 2. y'<0
Case 2.1 $\theta_t-\pi/2 > -\theta_0+\pi/2$ (Similar to FIG. 8A but with the location of P and $C_0$ interchanged)

PSF at P=(½)h(x,y;x',y';$-\theta_0+\pi$)+(½)h(x,y;x',y';$\pi$)

Case 2.2 $\theta_t-\pi/2 < -\theta_0+\pi/2$ (Similar to FIG. 8B but with the location of P and $C_0$ interchanged)

PSF at P=(½)h(x,y;x',y';$-\theta_0$)+(½)h(x,y;x',y';$\pi$)+h(x,y;x',y';$\theta_t$)

Summarizing, for the view angular range [0,$\pi$] measured from the spiral end we have shown that applying sub-steps (1) through (3) to any point on the detector results in a number of essentially 1D PSF h:

For the portion of the image above the x axis (Case 1. y'>0):
  No computation 16 For the portion of the image below the x axis (Case 2. y'<0):
  1 D Hilbert transform in the $-x$ direction [h(x,y;x',y';$\pi$)].
  Determine the point $C_0$ on the x axis where the current source position projects in the direction which projects the start source position onto the edge of the spiral cylinder.
  1 D Hilbert transform in the direction of the scan path the portion of the image below the x axis and to the right of the line (infinitely extended) $L_c$ through $C_0$ in the direction of the scan path [h(x,y;x',y';$\theta_t$)].
  1 D Hilbert transform along each line intersecting the point $C_0$ [h(x,y;x',y';$-\theta_0$) and h(x,y;x',y';$-\theta_0+\pi$)] respectively for the portions to the right and the left of the line $L_c$.

Since the above processing corresponds to the FBP substeps (1)–(3), it is still necessary to do sub-step (4), to complete the 2D processing steps. Since sub-step (4) is also a 1D operation, i.e. differentiating the backprojection image in the projected scan path direction t, the entire 2D step represented by Equation (1), in accordance with the present invention, is reduced to a number of 1D operations for the views near the 2 ends of the spiral scan, i.e. views in the first and the last 2$\pi$ angular range.

For the cone beam images acquired near the bottom of the ROI, i.e., the start of the scan path, the image processing is substantially the same as described above for processing cone beam images acquired near the top of the ROI, except that the sets of line segments shown FIGS. 3A and 3B that are bound by the x-axis and the bottom boundary of the mask, are now bound by the x-axis and the top boundary of the mask. This analysis can proceed in a similar manner to make corresponding modifications to the above description.

Thus, there has been shown and described a novel 3D CT imaging method and apparatus for obtaining an exact image reconstruction which eliminates the need for performing 2D projections and 2D backprojections for each $\theta$ onto the detector plane for the views of the ROI near the two ends of the spiral scan path, thereby greatly simplifying this portion of the FBP image reconstruction processing. Many changes, modifications, variations and other uses and applications of the subject invention will, however, become apparent to those skilled in the art after considering this specification and its accompanying drawings, which disclose a preferred embodiment thereof. For example, many alternative arrangements were noted in the above text. For example, the pitch of the spiral scan could be variable, instead of fixed, and the convolution processing could be done in the spatial frequency domain using the Fourier transform of the Hilbert kernal. Furthermore, although in the preferred embodiment the x-axis of the detector was coincident with the x-axis of the data-combination masks, such coincidence is not required, nor is it required to provide a complete blocking of the radiation exposure to one side of the axis (even a partial blocking of the radiation to one side of the axis would be desirable). All such changes, modifications, variations and other uses and applications which do not depart from the teachings herein are deemed to be covered by this patent, which is limited only by the claims which follow as interpreted in light of the foregoing description.

What is claimed is:

1. A method for performing three dimensional computerized tomographic imaging a region-of-interest (ROI) in an object using a cone beam source of radiation energy, comprising the steps of:

defining a source scan path that encircles the ROI in the object and is traversed by the cone beam source;

using the cone beam source, fixed relative to an area detector with both source and as detector movably positioned relative to the object, for applying radiation energy towards the object from a plurality of source positions along the scan path as said source traverses the scan path, said applying causing said area detector to acquire a set of cone beam projection data corresponding to a respective portion of the object at each of said source positions;

applying a mask to each set of the acquired projection data so that data inside the boundaries of each mask form a corresponding plurality of masked data sets;

calculating image data along each of the line segments L formed in the masked cone beam projection data acquired at each of said source positions, said calculating step comprising performing a plurality of one-dimensional (1D) convolving operations of the masked projection data along a respective group of the line segments L, the 1D convolving operation for each group of the line segments L developing an additive contribution to a new projection image; and 3D backprojecting the new projection image into a 3D space, thereby reconstructing a 3D image of the ROI in the object.

2. The method of claim 1, wherein at source positions near one of a top or bottom edge of the ROI, said mask is divided into separate portions using at least a horizontal line therein, each portion having a group of line segments L formed therein, along which said calculating step performs said convolving operations.

3. The method of claim 1, wherein the new projection image developed by the convolving operations spreads out the image data over an area greater than the area of the area detector.

4. The method of claim 2, wherein for masked data sets acquired near one edge of the ROI, a first group of the line segments L comprise a plurality of parallel line segments formed in the masked cone beam data which resides below the horizontal line in the mask.

5. The method of claim 4, wherein the first group of the line segments L are spatially oriented so as to be parallel to a projection of a tangent to the scan path at the source position which acquired the masked cone beam data set in which the convolving operations for the first group of the line segments L are being performed.

6. The method of claim 4, wherein for masked data sets acquired near one edge of the ROI, a second group of the line segments L comprise a plurality of parallel line segments L formed in the masked cone beam data which reside above and are spatially oriented so as to be parallel with the horizontal line in the mask.

7. The method of claim 6, wherein for masked data sets acquired near one edge of the ROI, a third group of the line segments L comprises a plurality of parallel line segments L formed in the masked cone beam data which reside above the horizontal axis in the mask and are spatially oriented so as to be parallel to a projection of a tangent to the scan path at the source position which acquired the masked cone beam data set in which the convolving operations for the third group of the line segments L are being performed.

8. The method of claim 7, wherein said third group of the line segments L are limited to a portion of the mask residing on one side of a point $C_0$ on the horizontal line in the mask in which the convolving operations for the third group of the line segments L are being performed.

9. The method of claim 7, wherein for masked data sets acquired near one edge of the ROI, a fourth group of the line segments L comprises a plurality of radially extending line segments L formed in the masked cone beam data which reside above the horizontal line in the mask and extend radially from or towards a point $C_0$ on the horizontal line in the mask in which the convolving operations for the fourth group of the line segments L are being performed.

10. The method of claim 2, including a d/dt processing step for filtering the new backprojection image before said 3D backprojection.

11. The method of claim 1, wherein said 1D convolving operations comprise Hilbert transformation operations.

12. The method of claim 2, wherein the line segments L of each group have a consistent spatial orientation with respect to each other, but the spatial orientation of the line segments of at least one group being different from the spatial orientation of the line segments L of another group.

13. The method of claim 2, wherein said masked cone beam data is divided into separate portions based on the location of a point $C_0$ determined on an axial line crossing the mask, which point $C_0$ is defined by an intersection of a projection onto the area detector of the source position which acquired the masked cone beam data and the axial line.

14. The method of claim 13, wherein the scan path has a longitudinal axis and the point $C_0$ is determined by:
  (a) determining a first line (406) which is tangent to the scan path (404) and perpendicular to its longitudinal axis;
  (b) determining a second line (410) which is parallel to the first line (406) and which passes through the source position ($S_i$) which acquired the data being masked; and
  (c) defining as point $C_0$ that point where the second line intersects the plane (412) of the detector.

15. A method for performing three dimensional computerized tomographic imaging near at least one of an upper or lower boundary of a region-of-interest (ROI) in an object using a cone beam source of radiation energy, comprising the steps of;
  defining a source scan path that encircles the ROI near one of the boundaries in the object and is traversed by the cone beam source;
  using the cone beam source, fixed relative to an area detector with both source and detector movably positioned relative to the object, for applying radiation energy towards the object from a plurality of source positions along the scan path as said source traverses the scan path, said applying causing said area detector to acquire a set of cone beam projection data corresponding to a respective portion of the object at each of said source positions;
  applying a mask to each set of the acquired projection data so that data inside each mask form a corresponding plurality of masked data sets;
  dividing those masked data sets acquired near a boundary of the ROI into a plurality of different spatial regions, one or more of said regions including a set of line segments L formed in the masked data which have a consistent spatial orientation with respect to each other, but with the line segments L of one region having a different spatial orientation with respect to the line segments L of another region;
  calculating image data along each of the line segments L formed in the masked cone beam projection data acquired at each of said source positions, said image data corresponding to an additive contribution to a new projection image; and
  3D backprojecting the new projection image into a 3D space, thereby reconstructing a 3D image of the ROI in the object.

16. The method of claim 15, wherein said calculating step comprises performing a plurality of one-dimensional (1D) convolving operations of the masked projection data along a respective group of the line segments L, the 1D convolving operation for each group of the line segments L developing the additive contribution to a new projection image.

17. The method of claim 16, wherein said 1D convolving operations comprise Hilbert transformation operations.

18. A method for performing three dimensional computerized tomographic imaging near a boundary of a region-of-interest (ROI) in an object using a cone beam source of radiation energy, comprising the steps of:
  defining a source scan path that encircles the ROI in the object and is traversed by the cone beam source;
  using the cone beam source, fixed relative to an area detector with both source and detector movably positioned relative to the object, for applying radiation energy towards the object from a plurality of source positions along the scan path as said source traverses the scan path, said applying causing said area detector to acquire a set of cone beam projection data corresponding to a respective portion of the object at each of said source positions;
  applying a mask to each set of the acquired projection data so that data inside the boundaries of each mask form a corresponding plurality of masked data sets;
  dividing those masked data sets acquired near a boundary of the ROI into a plurality of different spatial regions, one or more of said regions including a set of line segments L formed in the masked data which have a consistent spatial orientation with respect to each other, but with the line segments L of one region having a different spatial orientation with respect to the line segments L of another region;

calculating image data along each of said line segments L for developing an additive contribution to a new projection image; and 3D backprojecting the new projection image into a 3D space, thereby accurately reconstructing a 3D image of the boundary of the ROI in the object.

19. Apparatus for performing three dimensional computerized tomographic imaging near a boundary of a region-of-interest (ROI) in an object using a cone beam source of radiation energy, comprising:

a source of cone beam radiation energy;

a manipulator for providing a source scanning trajectory as a scan path that encircles the ROI in the object and causes the source and detector to traverse the scan path;

means for causing the source to apply radiation energy towards the object from a plurality of source positions along the scan path as said source traverses the scan path, said area detector acquiring cone beam projection data corresponding to respective portions of the object at each of said source positions; and an image reconstruction processor for, applying a mask to the cone beam projection data acquired at each of said source positions, dividing those masked data sets acquired near a boundary of the ROI into a plurality of different spatial regions, at least two of said regions each including a set of line segments L formed therein which have a consistent spatial direction relative to each other, wherein the spatial direction of the line segments L of one region are different from the spatial direction of the line segments L of another region;

calculating image data along each of said line segments L for developing an additive contribution to a new projection image; and 3D backprojecting the new projection image into a 3D space, thereby accurately reconstructing a 3D image of the boundary of the ROI in the object.

20. The apparatus of claim 19, wherein said image reconstruction processor calculates a plurality of one-dimensional (1D) convolving operations of the masked projection data along a respective group of the line segments L, the 1D convolving operation for each group of the line segments L developing the additive contribution to a new projection image.

21. The apparatus of claim 20, wherein said image reconstruction processor performs Hilbert transformation operations as said 1D convolving operations.

* * * * *